United States Patent
Lunner et al.

(10) Patent No.: US 11,785,397 B2
(45) Date of Patent: *Oct. 10, 2023

(54) HEARING AID COMPRISING A PHYSIOLOGICAL SENSOR

(71) Applicant: Oticon A/S, Smørum (DK)

(72) Inventors: Thomas Lunner, Redmond, WA (US); Tanveer Bhuiyan, Smørum (DK); José Antonio Esparza Isasa, Smørum (DK); Sergi Rotger Griful, Smørum (DK); Antonello Salvatucci, Billund (DK); Gary Jones, Smørum (DK); Kim Tilgaard Petersen, Smørum (DK); Peter Sommer, Smørum (DK)

(73) Assignee: Oticon A/S, Smørum (DK)

( * ) Notice: Subject to any disclaimer, the term of this patent is extended or adjusted under 35 U.S.C. 154(b) by 57 days.

This patent is subject to a terminal disclaimer.

(21) Appl. No.: 17/459,370

(22) Filed: Aug. 27, 2021

(65) Prior Publication Data

US 2021/0392446 A1 Dec. 16, 2021

Related U.S. Application Data

(62) Division of application No. 16/878,041, filed on May 19, 2020, now Pat. No. 11,134,351.

(51) Int. Cl.
*H04R 25/00* (2006.01)

(52) U.S. Cl.
CPC ......... *H04R 25/505* (2013.01); *H04R 25/554* (2013.01); *H04R 2225/41* (2013.01)

(58) Field of Classification Search
CPC . H04R 25/505; H04R 25/554; H04R 2225/41
(Continued)

(56) References Cited

U.S. PATENT DOCUMENTS

| | | | |
|---|---|---|---|
| 11,134,351 B1* | 9/2021 | Lunner | A61B 5/6817 |
| 2011/0150253 A1 | 6/2011 | Corona-Strauss et al. | |

(Continued)

FOREIGN PATENT DOCUMENTS

EP  3 492 002 A1  6/2019

OTHER PUBLICATIONS

Extended European Search Report for European Application No. 21172617.9, dated Sep. 17, 2021.
Esco et al., "Ultra-Short-Term Heart Rate Variability Indexes at Rest and Post-Exercise in Athletes: Evaluating the Agreement with Accepted Recommendations," Journal of Sports Science and Medicine, vol. 13, No. 3, 2014 (eCollection Sep. 1, 2014), pp. 535-541.
(Continued)

*Primary Examiner* — Phylesha Dabney
(74) *Attorney, Agent, or Firm* — Birch, Stewart, Kolasch & Birch, LLP

(57) ABSTRACT

The present application relates to a system comprising a hearing aid, the hearing aid configured to be operated based on an estimation of a current listening effort of a hearing aid user. The system comprising an input unit for receiving an input sound signal from an environment of the hearing aid user and providing at least one electric input signal representing said input sound signal, an output unit for providing at least one set of stimuli perceivable as sound to the hearing aid user based on processed versions of said at least one electric input signal, a signal-to-noise ratio (SNR) estimator for determining an SNR in the environment of the hearing aid user, a processing unit connected to said input unit and to said output unit and comprising signal processing parameters of the system to provide processed versions of said at least one electric input signal, a memory unit configured to store reference sets of SNR and pulse transition time (PTT) of the hearing aid user, at least a first and a second physiological sensor, wherein the system being configured to
(Continued)

determine, based on the first physiological sensor, a first point in time at a first maximum upslope point of a first measured parameter, determine, based on the second physiological sensor, a second point in time at a second maximum upslope point of a second measured parameter, establish a current PTT by calculating a time difference between the first point in time and the second point in time, and determine, based on the current PTT and the stored reference sets of SNR and PTT, a current listening effort of the hearing aid user.

18 Claims, 7 Drawing Sheets

(58) Field of Classification Search
USPC .......................................................... 381/315
See application file for complete search history.

(56) References Cited

U.S. PATENT DOCUMENTS

| | | |
|---|---|---|
| 2012/0203077 A1 | 8/2012 | He et al. |
| 2019/0052977 A1 | 2/2019 | Hannemann et al. |
| 2019/0174238 A1 | 6/2019 | Lunner |
| 2019/0182606 A1 | 6/2019 | Petersen et al. |

OTHER PUBLICATIONS

Goldberger, "Sympathovagal Balance: How Should We Measure It?" Am J Physiol., Apr;276(4 Pt 2), 1999, pp. H1273-H1280.

Hey et al., "Continuous Noninvasive Pulse Transit Time Measurement for Psycho-physiological Stress Monitoring," International Conference on eHealth, Telemedicine, and Social Medicine (TELEMED), Cancun, Mexico, 2009 (Feb. 2009), pp. 113-116 (total 5 pages).

Hoshi et al, "Poincaré Plot Indexes of Heart Rate Variability: Relationships with Other Nonlinear Variables," Autonomic Neuroscience: Basic and Clinical, vol. 177, 2013 (Jun. 2013), pp. 271-274 (total 5 pages).

Hsu et al., "Poincaré Plot Indexes of Heart Rate Variability Detect Dynamic Autonomic Modulation During General Anesthesia Induction," Acta Anaesthesiologica Taiwanica, vol. 50, No. 1, 2012, pp. 12-18.

Ohlenforst et al., "Impact of Stimulus-related Factors and Hearing Impairment on Listening Effort as Indicted by Pupil Dilation," Hearing Research, vol. 351, 2017 (Available online May 25, 2017), pp. 66-79.

Richter, "The Moderating Effect of Success Importance on the Relationship Between Listening Demand and Listening Effort," Ear & Hearing, vol. 37, Supplement 1, 2016, pp. 111S-117S.

* cited by examiner

HEARING AID COMPRISING A PHYSIOLOGICAL SENSOR

This application is a Divisional of co-pending application Ser. No. 16/878,041, filed on May 19, 2020, which is hereby expressly incorporated by reference into the present application.

SUMMARY

The present application relates to a hearing aid configured to be worn by a user at or in an ear of a user or to be fully or partially implanted in the head of a user. The present application further relates to a system.

A system:

The interest of incorporating different types of physiological sensors measuring one or more physiological signals, such as electrocardiogram (ECG), photoplethysmogram (PPG), electroencephalography (EEG), etc., of a user in systems (e.g. in systems comprising hearing aids) is increasing.

However, in systems comprising hearing aids, the application of the measurements of the physiological sensors to the audiological outcome of the hearing aids is not clear.

Listening effort has been shown to have physiological markers like pupillometry and heart parameters like PEP (pre-ejection period), but there is a lack of scientific evidence whether an ear level sensor (physiological sensors mounted in or at an ear or fully or partially implanted in the head of a user) can be used to estimate listening effort.

Further, currently, we do not take advantage of the fact that some hearing aid users have wearables with them all the time (e.g., smartwatch).

Accordingly, there is a need for an effort driven control of systems (or hearing aids) based on sensor data from the physiological sensor(s).

In an aspect of the present application, a system comprising a hearing aid is provided. The hearing aid may be configured to be operated based on an estimation of a current listening effort of a hearing aid user.

The system may comprise an input unit for receiving an input sound signal from an environment of a hearing aid user and providing at least one electric input signal representing said input sound signal.

Environment may refer to the surroundings, surrounding space of the hearing aid user.

The system may comprise an output unit for providing at least one set of stimuli perceivable as sound to the hearing aid user based on processed versions of said at least one electric input signal.

The system may comprise a signal-to-noise (SNR) ratio estimator for determining an SNR in the environment of the hearing aid user.

An SNR estimator may determine the SNR based on processed versions (e.g. provided by a processing unit) of said at least one electric input signal.

An SNR estimator may determine the SNR based on the at least one electric input signal from input unit.

An SNR estimator may determine the SNR based on (e.g. processed versions of) the at least one electric input signal from at least one input transducer, such as at least one microphone, of the input unit.

The system may comprise a processing unit.

The processing unit may be connected to said input unit.

The processing unit may be connected to said output unit.

The processing unit may comprise signal processing parameters of the system to provide processed versions of said at least one electric input signal.

The processing unit of the system may comprise the SNR estimator.

The system may comprise a memory unit.

The memory unit may be configured to store reference sets of SNR and pulse transition time (PTT) of the hearing aid user.

The reference sets of SNR and PTT may be individualised.

For example, reference sets of SNR and PTT may be determined based on a predetermined set of input sound signals exposed to the specific hearing aid user.

For example, the reference sets of SNR and PTT may be determined based on a predetermined set of input sound signals (e.g. talk and noise) exposed to a plurality of hearing aid users so that said reference sets comprise an interval of PTT values for each SNR value.

For example, the reference sets of SNR and PTT may be determined during a fitting session.

For example, the hearing aid may be configured to trigger a determination of PTT once in a while (e.g. with a time interval) when the user is in silence (in an environment with a low noise signal). Thereby, reference sets of SNR and PTT may be determined (baseline values). For example, a variation in the baseline values may indicate that the hearing aid user has been experiencing stress for a long time interval.

Thereby, a fast determination of a current listening effort of a hearing aid user is facilitated.

PTT may refer to the time it takes a pulse wave to travel between two arterial sites. It may be the time taken for the pulse wave to travel from the aortic valve to the periphery (i.e. measurement point, e.g. at least one of the ears).

Generally, it may be the time difference between the R-peak of an ECG and the maximum upslope point of a PPG signal. Prior art show that PTT has an inverse relationship with a person's exposure to stress [1].

Traditional PTT requires an ECG and an ear level PPG recording.

However, advantageously, PTT may be measured from two different point on the body e.g. from ear level PPG sensors, or e.g. from ear level ECG sensors (e.g. in-ear ECG sensors).

ECG and PPG based measurements of PTT may require an ear level sensor which can capture both ECG and PPG. On the other hand, a PPG sensor at each ear may be required for providing an ear to ear PTT signal.

For traditional PTT measurements utilizing ECG and PPG, a system may be mounted with sensor, e.g. TI AFE 4900, which may provide ECG and PPG signals and therefore can be used for ear level PTT measurements.

The system may comprise at least a first and a second physiological sensor. The first and second physiological sensors may be electrophysiological sensors.

For example, the at least first and second physiological sensors may comprise an ECG sensor, a PPG sensor, and/or an EEG sensor, etc.

The system may be configured to determine, based on the first physiological sensor, a first point in time at a first maximum upslope point of a first measured parameter.

The system may be configured to determine, based on the second physiological sensor, a second point in time at a second maximum upslope point of a second measured parameter.

The system may be configured to determine, based on the first physiological sensor, a first point in time at a maximum of a first derivative of a first measured parameter.

The system may be configured to determine, based on the second physiological sensor, a second point in time at a maximum of a first derivative of a second measured parameter.

The system may be configured to establish a current PTT by calculating a time difference between the first point in time and the second point in time.

For example, the system may be configured to establish a current PTT by calculating a time difference between two consecutive time instances of systolic pressure of the hearing aid user.

The system may be configured to establish a current PTT by cross correlating a first signal (e.g. waveform) measured by the first physiological sensor with a second signal (e.g. waveform) measured by the second physiological sensor.

For example, the maximum lag of the cross correlation may be approximately 100 ms, meaning that we may be looking for current PTT (e.g. binaural PTT (BinPTT)) less than 100 ms.

The cross correlation may be carried out based on said signals selected from a short time interval (e.g. 60 s). Thereby, an average of the current PTT may be determined resulting in a stabilised estimate of the current PTT.

The system may be configured to establish a current PTT by estimating the time difference (time delay) between the first and the second signals.

The system may be configured to determine, based on the current PTT and the stored reference sets of SNR and PTT, a current listening effort of the hearing aid user.

Thereby, the optimal hearing aid settings (signal processing parameters) may be determined and applied depending the listening effort of the hearing aid user.

The reference sets of SNR and PTT may be updated and/or adjusted when the system determines a set of SNR and corresponding current PTT. The system may be configured to update and/or adjust the reference sets of SNR and PTT stored in the memory unit of the system based on said set of SNR and corresponding current PTT.

For example, the updating and/or adjusting of said reference sets may be carried out based on machine learning (e.g. by use of a neural network such as a deep neural network).

The system being configured to determine the current listening effort may comprise to determine a current listening difficulty area.

Four listening difficulty areas may be defined.

A first listening difficulty area may be defined as having an SNR above a first SNR threshold and a PTT above a first PTT threshold. For example, in the first area, the PTT may be decreasing as a function of decreasing SNR. The first area may be indicative of the hearing aid user providing only little listening effort, as the SNR is high.

A second listening difficulty area may be defined as having an SNR below the first SNR threshold, and above a second SNR threshold, and a PTT below the first PTT threshold. For example, in the second area, the PTT may be decreasing as a function of decreasing SNR. The second area may be indicative of the hearing aid user is providing an increasing listening effort. A third listening difficulty area may be defined as having an SNR below the second SNR threshold, and above a third SNR threshold, and a PTT below the first PTT threshold. For example, in the third area, the PTT may be increasing as a function of decreasing SNR. The third area may be indicative of the hearing aid user starting to disengage and providing a decreasing listening effort.

A fourth listening difficulty area may be defined as having an SNR below the third SNR threshold and a PTT above the first PTT threshold. For example, in the fourth area, the PTT may be increasing as a function of decreasing SNR. The fourth area may be indicative of the hearing aid user completely disengaging and providing minimal listening effort.

The system may be configured to be in a first listening mode when the current listening difficulty area is the first area, a second listening mode when the current listening difficulty area is the second area, a third listening mode when the current listening difficulty area is the third area, and in a fourth listening mode when the current listening difficulty area is the fourth area.

Thereby, a characterisation of the current listening effort of the hearing aid user depending on the PTT determined by the at least first and second physiological sensors and the SNR estimator is provided.

To determine a current listening effort of the hearing aid user may comprise determining the listening mode of the system.

The system may be configured to adjust the signal processing parameters of the processing unit based on the determined current listening effort.

Adjusting the signal processing parameters of the processing unit may comprise adjusting noise reduction of the system.

Adjusting the signal processing parameters of the processing unit may comprise adjusting the gain of the system.

Adjusting the signal processing parameters of the processing unit may comprise adjusting the directionality of the system.

Adjusting the signal processing parameters of the processing unit may comprise adjusting the enhancement (e.g. spectral shaping) of the system.

The system may comprise a first wearable device.

The system may comprise a second wearable device.

The system may comprise a first wearable device and a second wearable device.

The first wearable device may comprise the first physiological sensor.

The second wearable device comprises the second physiological sensor.

The first and/or second wearable device may be a device/aid configured to be worn on the body of the hearing aid user. The first and/or second wearable device may be a hearing aid and/or a watch and/or a sensor device.

The system may comprise at least one accelerometer. The accelerometer may be configured to detect a movement of the hearing aid user. The accelerometer may be configured to detect movement in a vertical and/or in a horizontal direction. The accelerometer may be configured to detect the movement and/or acceleration and/or orientation and/or position of the hearing aid.

The system (e.g. the processing unit of the system) may be configured to determine whether an activation requirement is fulfilled.

Activation requirement may refer to that one or more conditions have to be fulfilled.

Accordingly, may refer to one or more thresholds, limits, boundaries, etc, have to be fulfilled before activation may take place.

The activation requirement may comprise that the movement detected by the accelerometer is below a first movement threshold.

The first movement threshold may refer to the accelerometer detecting no, a limited amount of movements per time unit, or only movements of a limited size/degree. Detecting movements with a limited size or amount would indicate that the hearing aid user may be standing still or at least is located in the approximate same area.

The accelerometer may be below the first movement threshold when no movement is detected. The accelerometer may be below the first movement threshold when movement is detected less than 200 counts/min.

For example, the hearing aid user may be standing in a room together with multiple other persons. While trying to have a conversation with one of the other persons or while trying to follow a presentation, the hearing aid user may be moving slightly around resulting in movements of limited amount per time unit or of limited size. The hearing aid user may be, however, located at the approximate same area.

The activation requirement may comprise that the SNR is below a fourth threshold.

The fourth threshold may refer to the power of the signal relative to the power of the noise in the environment of the hearing aid user being at a level where the user cannot hear another person speaking sufficiently clear and/or where the speech intelligibility is too low.

The SNR may be below the fourth threshold when the SNR is below 0 dB.

The SNR may be below the fourth threshold when the SNR is below −5 dB.

In response to the activation requirement being fulfilled, the processing unit may be configured to change the activation mode of the at least one first and second physiological sensor.

Thereby, power consumption of the system may be minimized, as the activation mode (and thus power consumption) of the at least one first and second physiological sensor may be controlled based on the movement of the user and of the environment the user is in.

Configured to change the activation mode of the at least first and second physiological sensor may comprise configured to activate the at least first and second physiological sensor.

For example, when the hearing aid user suddenly stands still (i.e. no movement is detected) to have a conversation with another person in a noisy environment (i.e. SNR is low), then it may be required to activate the first and second physiological sensor to determine listening effort and thus a possible required change of signal processing parameters of the system (e.g. of hearing aids in the system).

Configured to change the activation mode of the at least first and second physiological sensor may comprise configured to change the activation mode of the at least first and second physiological sensor from standby mode to operational mode.

When the activation requirement is not fulfilled, the processing unit may be configured to change or maintain the mode of the at least first and second physiological sensors to the standby mode or a deactivated mode.

A deactivated mode may refer to a shut down or power off mode. When the first and second physiological sensors are deactivated, the power consumption of the sensors are zero.

Providing that the first and second physiological sensors may be configured to be in a standby mode, when the activation requirement is not fulfilled, the power consumption of the sensors may be kept at a minimum, while the sensors may be rapidly changed to an operational mode immediately after the activation requirement is fulfilled. Rapid operationally functioning sensors are advantageous to provide the hearing aid user an optimal signal processing and/or to detect and/or to monitor physiological parameters of the hearing aid user when relevant.

The first wearable device and/or the second wearable device may be a hearing aid. Accordingly, the system may comprise a first hearing aid and/or a second hearing aid.

The first wearable device and/or the second wearable device may be a headset.

The first wearable device and/or the second wearable device may be an earphone.

The first wearable device and/or the second wearable device may be an ear protection device.

The first wearable device and/or the second wearable device may comprise a combination of a hearing aid, a headset, an earphone, and/or an ear protection device.

The system may comprise a first hearing aid and/or a second hearing aid.

The first hearing aid may comprise the first physiological sensor.

The second hearing aid may comprise the second physiological sensor.

The first and/or the second physiological sensor may be a PPG sensor.

A PPG sensor may provide a non-invasive monitoring of physiological parameters of the hearing aid user. A PPG sensor may be advantageous to use to monitor the heart rate of the hearing aid user.

Each of the first and second hearing aids may include an antenna and a transceiver circuitry for establishing a communication link to the other hearing aid, and thereby allowing the exchange of information between the two hearing aids.

Thereby, a PTT value may be determined based on a first physiological sensor in a first hearing aid and a second physiological sensor in a second hearing aid. For example, the first and second hearing aids may be arranged in respective right and left ears of the user.

A Hearing Aid

In an aspect of the present application, a hearing aid configured to be worn by a user at or in an ear of a user or to be fully or partially implanted in the head of a user is provided.

The hearing aid may comprise an input unit for receiving an input sound signal from an environment of a hearing aid user and providing at least one electric input signal representing said input sound signal.

The hearing aid may comprise an output unit for providing at least one set of stimuli perceivable as sound to the user based on processed versions of said at least one electric input signal.

The hearing aid may comprise an accelerometer. The accelerometer may be configured to detect a movement of the hearing aid.

The hearing aid may comprise an SNR estimator for determining the SNR in the environment of the hearing aid (hearing aid user).

An SNR estimator may determine the SNR based on processed versions (e.g. provided by a processing unit) of said at least one electric input signal.

An SNR estimator may determine the SNR based on the at least one electric input signal from input unit.

An SNR estimator may determine the SNR based on (e.g. processed versions of) the at least one electric input signal from at least one input transducer, such as at least one microphone, of the input unit.

The hearing aid may comprise a processing unit.

The processing unit may be connected to said input unit.

The processing unit may be connected to said output unit.

The processing unit may comprise signal processing parameters of the hearing aid to provide processed versions of said at least one electric input signal.

The processing unit may comprise the SNR estimator.

The processing unit may be configured to determine whether an activation requirement is fulfilled.

Activation requirement may refer to that one or more conditions have to be fulfilled. Accordingly, may refer to one or more thresholds, limits, boundaries, etc., have to be fulfilled before activation may take place.

The activation requirement may comprise that the movement detected by the accelerometer is below a first movement threshold.

The first movement threshold may refer to the accelerometer detecting no, a limited amount of movements per time unit, or only movements of a limited size/degree. Detecting movements with a limited size or amount would indicate that the hearing aid user may be standing still or at least is located at the approximate same area.

The accelerometer may be below the first movement threshold when no movement is detected. The accelerometer may be below the first movement threshold when movement is detected less than 200 counts/min.

The activation requirement may comprise that the SNR is below a fourth threshold.

The fourth threshold may refer to the power of the signal relative to the power of the noise in the environment of the hearing aid user being at a level where the user cannot hear another person speaking sufficiently clear and/or where the speech intelligibility is too low.

The SNR may be below the fourth threshold when the SNR is below 0 dB.

The SNR may be below the fourth threshold when the SNR is below −5 dB.

In response to the activation requirement being fulfilled, the processing unit may be configured to change the mode of at least one PPG sensor of the hearing aid.

The processing unit may be configured to automatically change the mode of the PPG sensor, in response to the activation requirement being fulfilled.

Advantageously, changing the mode of the PPG sensor or any other type of sensor may be done when the movement detected by the accelerometer is below a first threshold. This could, for example, indicate that the hearing aid user is relatively passive or standing still, so that changes in the heart rate of the hearing aid user is not caused by changes in the physical activity of the hearing aid user, but may rather be caused by a change in the level of stress, concentration, etc.

The processing unit being configured to change the mode of the at least one PPG sensor may comprise being configured to activate the at least one PPG sensor.

The processing unit being configured to change the mode of the at least one PPG sensor may comprise being configured to change the mode of the at least one PPG sensor from standby mode to operational mode.

The hearing aid may comprise a switch configured to control the changing of the mode of the at least one PPG sensor.

Providing that the PPG sensor is activated and/or changed/switched to an operational mode only in response to the activation requirement being fulfilled, has the advantage that the power consumption of the PPG sensor(s) and thus of the hearing aid is kept at a minimum. Keeping the power consumption of the hearing aid as such at a minimum is of great importance to provide a stable functioning hearing aid, and so that the hearing aid may provide sufficient energy for a wide range of signal processing schedules and a large number of sensors.

Providing that the PPG sensor may be configured to be turned off, when the activation requirement is not fulfilled, the power consumption of the PPG sensor may be kept at a minimum.

Providing that the PPG sensor may be configured to be in a standby mode, when the activation requirement is not fulfilled, the power consumption of the PPG sensor may be kept at a minimum, while the PPG sensor may be rapidly changed to an operational mode immediately after the activation requirement is fulfilled. A rapid operationally functioning PPG sensor is advantageous to provide the hearing aid user an optimal signal processing and/or to detect and/or to monitor physiological parameters of the hearing aid user when relevant.

In response to the activation requirement being fulfilled, the processing unit may be configured to alter the signal processing parameters of the hearing aid.

Altering the signal processing parameters of the hearing aid may comprise one or more of increasing the noise reduction, changing the gain, changing the directionality, and/or enhancement (e.g. spectral shaping).

When the activation requirement is not fulfilled, the processing unit may be configured to change the mode of the at least one PPG sensor to the standby mode.

For example, the activation requirement may not be fulfilled any more (and use of the PPG sensors may not be relevant) when the hearing aid user is walking from one place to another. Thus, the mode of the at least one PPG sensor may advantageously be changed to the standby mode during the walking in order to reduce power consumption, but on standby mode to be rapidly activated again, when the activation requirement is fulfilled (again).

When the activation requirement is not fulfilled, the processing unit may be configured to change the mode of the at least one PPG sensor to a deactivated mode.

For example, when the activation requirement has not been fulfilled for long, which may be the case when the user is active and/or the SNR is at a high level for long, the at least one PPG sensor may be deactivated to reduce power consumption (compared to the standby mode).

When the activation requirement is not fulfilled, the processing unit may be configured to maintain the mode of the at least one PPG sensor at the standby mode.

For example, as long as the activation requirement is not fulfilled, the PPG sensor may be maintained at the standby mode.

When the activation requirement is not fulfilled, the processing unit may be configured to maintain the mode of the at least one PPG sensor at a deactivated mode.

For example, as long as the activation requirement is not fulfilled, the PPG sensor may be maintained at a deactivated mode.

The hearing aid may be replaced by a headset.

The hearing aid may be replaced by an earphone.

The hearing aid may be replaced by an ear protection device.

The hearing aid may be constituted by or comprise a combination of a hearing aid, a headset, an earphone, and/or an ear protection device.

In an aspect of the present application, a binaural system is provided.

The binaural system may comprise two hearing aids as described above.

For example, one or both of the hearing aids may comprise an accelerometer, and one or both of the hearing aids may comprise at least one PPG sensor.

Each hearing aid may further include an antenna and a transceiver circuitry for establishing a communication link to the other hearing aid. Thereby, exchange of information between the two hearing aids is allowed. The information to be exchanged may comprise information regarding the respective PPG and/or accelerometer measurements, and/or the signal processing to be carried out e.g. based on the PPG and/or accelerometer measurements. The processing unit carrying out the signal processing may be one or both of the processing units of the two hearing aids of the binaural system.

The hearing aid may be adapted to provide a frequency dependent gain and/or a level dependent compression and/or a transposition (with or without frequency compression) of one or more frequency ranges to one or more other frequency ranges, e.g. to compensate for a hearing impairment of a user. The hearing aid may comprise a signal processor for enhancing the input signals and providing a processed output signal.

The hearing aid may comprise an output unit for providing a stimulus perceived by the user as an acoustic signal based on a processed electric signal. The output unit may comprise a number of electrodes of a cochlear implant (for a CI type hearing device/aid) or a vibrator of a bone conducting hearing aid. The output unit may comprise an output transducer. The output transducer may comprise a receiver (loudspeaker) for providing the stimulus as an acoustic signal to the user (e.g. in an acoustic (air conduction based) hearing aid). The output transducer may comprise a vibrator for providing the stimulus as mechanical vibration of a skull bone to the user (e.g. in a bone-attached or bone-anchored hearing aid).

The hearing aid may comprise an input unit for providing an electric input signal representing sound. The input unit may comprise an input transducer, e.g. a microphone, for converting an input sound to an electric input signal. The input unit may comprise a wireless receiver for receiving a wireless signal comprising or representing sound and for providing an electric input signal representing said sound. The wireless receiver may e.g. be configured to receive an electromagnetic signal in the radio frequency range (3 kHz to 300 GHz). The wireless receiver may e.g. be configured to receive an electromagnetic signal in a frequency range of light (e.g. infrared light 300 GHz to 430 THz, or visible light, e.g. 430 THz to 770 THz).

The hearing aid may comprise a directional microphone system adapted to spatially filter sounds from the environment, and thereby enhance a target acoustic source among a multitude of acoustic sources in the local environment of the user wearing the hearing aid. The directional system is adapted to detect (such as adaptively detect) from which direction a particular part of the microphone signal originates. This can be achieved in various different ways as e.g. described in the prior art. In hearing aids, a microphone array beamformer is often used for spatially attenuating background noise sources. Many beamformer variants can be found in literature. The minimum variance distortionless response (MVDR) beamformer is widely used in microphone array signal processing. Ideally, the MVDR beamformer keeps the signals from the target direction (also referred to as the look direction) unchanged, while attenuating sound signals from other directions maximally. The generalized sidelobe canceller (GSC) structure is an equivalent representation of the MVDR beamformer offering computational and numerical advantages over a direct implementation in its original form.

The hearing aid may comprise antenna and transceiver circuitry (e.g. a wireless receiver) for wirelessly receiving a direct electric input signal from another device, e.g. from an entertainment device (e.g. a TV-set), a communication device, a wireless microphone, or another hearing aid. The direct electric input signal may represent or comprise an audio signal and/or a control signal and/or an information signal. The hearing aid may comprise demodulation circuitry for demodulating the received direct electric input to provide the direct electric input signal representing an audio signal and/or a control signal e.g. for setting an operational parameter (e.g. volume) and/or a processing parameter of the hearing aid. In general, a wireless link established by antenna and transceiver circuitry of the hearing aid can be of any type. The wireless link is established between two devices/aids, e.g. between an entertainment device (e.g. a TV) and the hearing aid, or between two hearing aids, e.g. via a third, intermediate device (e.g. a processing device, such as a remote control device, a smartphone, etc.). The wireless link is used under power constraints, e.g. in that the hearing aid may be constituted by or comprise a portable (typically battery driven) device. The wireless link is a link based on near-field communication, e.g. an inductive link based on an inductive coupling between antenna coils of transmitter and receiver parts. The wireless link may be based on far-field, electromagnetic radiation. The communication via the wireless link is arranged according to a specific modulation scheme, e.g. an analogue modulation scheme, such as FM (frequency modulation) or AM (amplitude modulation) or PM (phase modulation), or a digital modulation scheme, such as ASK (amplitude shift keying), e.g. On-Off keying, FSK (frequency shift keying), PSK (phase shift keying), e.g. MSK (minimum shift keying), or QAM (quadrature amplitude modulation), etc.

The communication between the hearing aid and the other device may be in the base band (audio frequency range, e.g. between 0 and 20 kHz). Preferably, communication between the hearing aid and the other device is based on some sort of modulation at frequencies above 100 kHz. Preferably, frequencies used to establish a communication link between the hearing aid and the other device is below 70 GHz, e.g. located in a range from 50 MHz to 70 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). The wireless link is based on a standardized or proprietary technology. The wireless link is based on Bluetooth technology (e.g. Bluetooth Low-Energy technology).

The hearing aid and/or the communication device may comprise an electrically small antenna. An 'electrically small antenna' is in the present context taken to mean that the spatial extension of the antenna (e.g. the maximum physical dimension in any direction) is much smaller than the wavelength $\lambda_{Tx}$ of the transmitted electric signal. The spatial extension of the antenna is a factor of 10, or 50 or 100 or more, or a factor of 1000 or more, smaller than the carrier wavelength $\lambda_{Tx}$ of the transmitted signal. The hearing aid is a relatively small device. The term 'a relatively small device' is in the present context taken to mean a device whose maximum physical dimension (and thus of an antenna for providing a wireless interface to the device) is smaller than 10 cm, such as smaller than 5 cm. In the present context, 'a relatively small device' may be a device whose maximum physical dimension is much smaller (e.g. more than 3 times, such as more than 10 times smaller, such as more than 20 times small) than the operating wavelength of a wireless interface to which the antenna is intended (ideally an antenna for radiation of electromagnetic waves at a given frequency should be larger than or equal to half the wavelength of the radiated waves at that frequency). At 860 MHz, the wavelength in vacuum is around 35 cm. At 2.4 GHz, the wavelength in vacuum is around 12 cm. The hearing aid has a maximum outer dimension of the order of 0.15 m (e.g. a handheld mobile telephone). The hearing aid has a maximum outer dimension of the order of 0.08 m (e.g. a head set). The hearing aid has a maximum outer dimension of the order of 0.04 m (e.g. a hearing instrument).

The hearing aid may be or form part of a portable (i.e. configured to be wearable) device, e.g. a device comprising a local energy source, e.g. a battery, e.g. a rechargeable battery. The hearing aid may e.g. be a low weight, easily wearable, device, e.g. having a total weight less than 100 g.

The hearing aid may comprise a forward or signal path between an input unit (e.g. an input transducer, such as a microphone or a microphone system and/or direct electric input (e.g. a wireless receiver)) and an output unit, e.g. an output transducer. The signal processor is located in the forward path. The signal processor is adapted to provide a frequency dependent gain according to a user's particular needs. The hearing aid may comprise an analysis path comprising functional components for analyzing the input signal (e.g. determining a level, a modulation, a type of signal, an acoustic feedback estimate, etc.). Some or all signal processing of the analysis path and/or the signal path may be conducted in the frequency domain. Some or all signal processing of the analysis path and/or the signal path may be conducted in the time domain.

An analogue electric signal representing an acoustic signal may be converted to a digital audio signal in an analogue-to-digital (AD) conversion process, where the analogue signal is sampled with a predefined sampling frequency or rate $f_s$, $f_s$ being e.g. in the range from 8 kHz to 48 kHz (adapted to the particular needs of the application) to provide digital samples $x_n$ (or x[n]) at discrete points in time $t_n$ (or n), each audio sample representing the value of the acoustic signal at $t_n$ by a predefined number $N_b$ of bits, $N_b$ being e.g. in the range from 1 to 48 bits, e.g. 24 bits. Each audio sample is hence quantized using $N_b$ bits (resulting in $2^{Nb}$ different possible values of the audio sample). A digital sample x has a length in time of $1/f_s$, e.g. 50 µs, for $f_s$=20 kHz. A number of audio samples may be arranged in a time frame. A time frame may comprise 64 or 128 audio data samples. Other frame lengths may be used depending on the practical application.

The hearing aid may comprise an analogue-to-digital (AD) converter to digitize an analogue input (e.g. from an input transducer, such as a microphone) with a predefined sampling rate, e.g. 20 kHz. The hearing aids comprise a digital-to-analogue (DA) converter to convert a digital signal to an analogue output signal, e.g. for being presented to a user via an output transducer.

The hearing aid, e.g. the input unit, and or the antenna and transceiver circuitry comprise(s) a TF-conversion unit for providing a time-frequency representation of an input signal. The time-frequency representation may comprise an array or map of corresponding complex or real values of the signal in question in a particular time and frequency range. The TF conversion unit may comprise a filter bank for filtering a (time varying) input signal and providing a number of (time varying) output signals each comprising a distinct frequency range of the input signal. The TF conversion unit may comprise a Fourier transformation unit for converting a time variant input signal to a (time variant) signal in the (time-) frequency domain. The frequency range considered by the hearing aid from a minimum frequency $f_{min}$ to a maximum frequency $f_{max}$ may comprise a part of the typical human audible frequency range from 20 Hz to 20 kHz, e.g. a part of the range from 20 Hz to 12 kHz. Typically, a sample rate $f_s$ is larger than or equal to twice the maximum frequency $f_{max}$, $f_s \geq 2f_{max}$. A signal of the forward and/or analysis path of the hearing aid may be split into a number NI of frequency bands (e.g. of uniform width), where NI is e.g. larger than 5, such as larger than 10, such as larger than 50, such as larger than 100, such as larger than 500, at least some of which are processed individually. The hearing aid is/are adapted to process a signal of the forward and/or analysis path in a number NP of different frequency channels (NP≤NI). The frequency channels may be uniform or non-uniform in width (e.g. increasing in width with frequency), overlapping or non-overlapping.

The hearing aid may be configured to operate in different modes, e.g. a normal mode and one or more specific modes, e.g. selectable by a user, or automatically selectable. A mode of operation may be optimized to a specific acoustic situation or environment. A mode of operation may include a low-power mode, where functionality of the hearing aid is reduced (e.g. to save power), e.g. to disable wireless communication, and/or to disable specific features of the hearing aid.

The hearing aid may comprise a number of detectors configured to provide status signals relating to a current physical environment of the hearing aid (e.g. the current acoustic environment), and/or to a current state of the user wearing the hearing aid, and/or to a current state or mode of operation of the hearing aid. Alternatively, or additionally, one or more detectors may form part of an external device in communication (e.g. wirelessly) with the hearing aid. An external device may e.g. comprise another hearing aid, a remote control, and audio delivery device, a telephone (e.g. a smartphone), an external sensor, etc.

One or more of the number of detectors may operate on the full band signal (time domain). One or more of the number of detectors may operate on band split signals ((time-) frequency domain), e.g. in a limited number of frequency bands.

The number of detectors may comprise a level detector for estimating a current level of a signal of the forward path. The detector may be configured to decide whether the current level of a signal of the forward path is above or below a given (L-)threshold value. The level detector operates on the full band signal (time domain). The level detector operates on band split signals ((time-) frequency domain).

The hearing aid may comprise a voice activity detector (VAD) for estimating whether or not (or with what probability) an input signal comprises a voice signal (at a given point in time). A voice signal is in the present context taken to include a speech signal from a human being. It may also include other forms of utterances generated by the human speech system (e.g. singing). The voice activity detector unit is adapted to classify a current acoustic environment of the user as a VOICE or NO-VOICE environment. This has the advantage that time segments of the electric microphone signal comprising human utterances (e.g. speech) in the user's environment can be identified, and thus separated from time segments only (or mainly) comprising other sound sources (e.g. artificially generated noise). The voice activity detector may be adapted to detect as a VOICE also the user's own voice. Alternatively, the voice activity detector may be adapted to exclude a user's own voice from the detection of a VOICE.

The hearing aid may comprise an own voice detector for estimating whether or not (or with what probability) a given input sound (e.g. a voice, e.g. speech) originates from the voice of the user of the system. A microphone system of the hearing aid may be adapted to be able to differentiate between a user's own voice and another person's voice and possibly from NON-voice sounds.

The number of detectors may comprise a movement detector, e.g. an acceleration sensor. The movement detector is configured to detect movement of the user's facial muscles and/or bones, e.g. due to speech or chewing (e.g. jaw movement) and to provide a detector signal indicative thereof.

The hearing aid may comprise a classification unit configured to classify the current situation based on input signals from (at least some of) the detectors, and possibly other inputs as well. In the present context 'a current situation' is taken to be defined by one or more of
a) the physical environment (e.g. including the current electromagnetic environment, e.g. the occurrence of electromagnetic signals (e.g. comprising audio and/or control signals) intended or not intended for reception by the hearing aid, or other properties of the current environment than acoustic);
b) the current acoustic situation (input level, feedback, etc.), and
c) the current mode or state of the user (movement, temperature, cognitive load, etc.);
d) the current mode or state of the hearing aid (program selected, time elapsed since last user interaction, etc.) and/or of another device in communication with the hearing aid.

The classification unit may be based on or comprise a neural network, e.g. a trained neural network.

The hearing aid may comprise an acoustic (and/or mechanical) feedback control (e.g. suppression) or echo-cancelling system. Acoustic feedback occurs because the output loudspeaker signal from an audio system providing amplification of a signal picked up by a microphone is partly returned to the microphone via an acoustic coupling through the air or other media. The part of the loudspeaker signal returned to the microphone is then re-amplified by the system before it is re-presented at the loudspeaker, and again returned to the microphone. As this cycle continues, the effect of acoustic feedback becomes audible as artifacts or even worse, howling, when the system becomes unstable. The problem appears typically when the microphone and the loudspeaker are placed closely together, as e.g. in hearing aids or other audio systems. Some other classic situations with feedback problems are telephony, public address systems, headsets, audio conference systems, etc. Adaptive feedback cancellation has the ability to track feedback path changes over time. It is based on a linear time invariant filter to estimate the feedback path but its filter weights are updated over time. The filter update may be calculated using stochastic gradient algorithms, including some form of the Least Mean Square (LMS) or the Normalized LMS (NLMS) algorithms. They both have the property to minimize the error signal in the mean square sense with the NLMS additionally normalizing the filter update with respect to the squared Euclidean norm of some reference signal.

The feedback control system may comprise a feedback estimation unit for providing a feedback signal representative of an estimate of the acoustic feedback path, and a combination unit, e.g. a subtraction unit, for subtracting the feedback signal from a signal of the forward path (e.g. as picked up by an input transducer of the hearing aid). The feedback estimation unit may comprise an update part comprising an adaptive algorithm and a variable filter part for filtering an input signal according to variable filter coefficients determined by said adaptive algorithm, wherein the update part is configured to update said filter coefficients of the variable filter part with a configurable update frequency $f_{upd}$. The hearing aid is configured to provide that the configurable update frequency $f_{upd}$ has a maximum value $f_{upd,max}$. The maximum value $f_{upd,max}$ is a fraction of a sampling frequency $f_s$ of an AD converter of the hearing aid ($f_{upd,max}=f_s/D$).

The update part of the adaptive filter may comprise an adaptive algorithm for calculating updated filter coefficients for being transferred to the variable filter part of the adaptive filter. The timing of calculation and/or transfer of updated filter coefficients from the update part to the variable filter part may be controlled by the activation control unit. The timing of the update (e.g. its specific point in time, and/or its update frequency) may preferably be influenced by various properties of the signal of the forward path. The update control scheme is preferably supported by one or more detectors of the hearing aid, preferably included in a predefined criterion comprising the detector signals.

The hearing aid may further comprise other relevant functionality for the application in question, e.g. compression, noise reduction, etc.

The hearing aid may be replaced by a hearing device which may comprise a listening device, e.g. a hearing aid, e.g. a hearing instrument, e.g. a hearing instrument adapted for being located at the ear or fully or partially in the ear canal of a user, e.g. a headset, an earphone, an ear protection device or a combination thereof. The hearing assistance system may comprise a speakerphone (comprising a number of input transducers and a number of output transducers, e.g. for use in an audio conference situation), e.g. comprising a beamformer filtering unit, e.g. providing multiple beam-forming capabilities.

Use:

In an aspect, use of a hearing aid as described above, in the 'detailed description of embodiments' and in the claims, is moreover provided. Use may be provided in a system comprising audio distribution. Use may be provided in a system comprising one or more hearing aids (e.g. hearing instruments), headsets, ear phones, active ear protection systems, etc., e.g. in handsfree telephone systems, teleconferencing systems (e.g. including a speakerphone), public address systems, karaoke systems, classroom amplification systems, etc.

A method:

In an aspect of the present application, a method of operating a system comprising a hearing aid based on an estimation of a current listening effort of a hearing aid user is provided.

The method may comprise receiving an input sound signal from an environment of the hearing aid user and providing at least one electric input signal representing said input sound signal by an input unit.

The method may comprise providing at least one set of stimuli perceivable as sound to the hearing aid user based on processed versions of said at least one electric input signal by an output unit.

The method may comprise determining a signal-to-noise ratio (SNR) in the environment of the hearing aid user by an SNR estimator.

The method may comprise providing processed versions of said at least one electric input signal by a processing unit connected to said input unit and to said output unit and comprising signal processing parameters of the system.

The method may comprise storing reference sets of SNR and pulse transition time (PTT) of the hearing aid user by a memory unit.

The method may comprise providing at least a first and a second physiological sensor.

The method may comprise determining, based on the first physiological sensor, a first point in time at a first maximum upslope point of a first measured parameter.

The method may comprise determining, based on the second physiological sensor, a second point in time at a second maximum upslope point of a second measured parameter.

The method may comprise establishing a current PTT by calculating a time difference between the first point in time and the second point in time.

The method may comprise determining, based on the current PTT and the stored reference sets of SNR and PTT, a current listening effort of the hearing aid user.

In an aspect of the present application, a method of operating a system based on an estimation of a current listening effort of a hearing aid user being monitored by a first physiological sensor and a second physiological sensor is provided.

The method may comprise determining, based on the first physiological sensor, a first point in time at a first maximum upslope point of a first measured parameter.

The method may comprise determining, based on the second physiological sensor, a second point in time at a second maximum upslope point of a second measured parameter.

The method may comprise establishing a current PTT by calculating a time difference between the first point in time and the second point in time.

The method may comprise determining, based on the current PTT as a function of signal-to-noise ratio (SNR), a current listening difficulty area, wherein four listening difficulty areas are defined.

A first area may be defined as having an SNR above a first SNR threshold and a PTT above a first PTT threshold.

A second area may be defined as having an SNR below the first SNR threshold, and above a second SNR threshold, and a PTT below the first PTT threshold.

A third area may be defined as having an SNR below the second SNR threshold, and above a third SNR threshold, and a PTT below the first PTT threshold.

A fourth area may be defined as having an SNR below the third SNR threshold and a PTT above the first PTT threshold.

The system may be configured to be in a first listening mode when the current listening difficulty area is the first area, a second listening mode when the current listening difficulty area is the second area, a third listening mode when the current listening difficulty area is the third area, and in a fourth listening mode when the current listening difficulty area is the fourth area.

It is intended that some or all of the structural features of the aid described above, in the 'detailed description of embodiments' or in the claims can be combined with embodiments of the method, when appropriately substituted by a corresponding process and vice versa. Embodiments of the method have the same advantages as the corresponding devices.

A Computer Readable Medium or Data Carrier:

In an aspect, a tangible computer-readable medium (a data carrier) storing a computer program comprising program code means (instructions) for causing a data processing system (a computer) to perform (carry out) at least some (such as a majority or all) of the (steps of the) method described above, in the 'detailed description of embodiments' and in the claims, when said computer program is executed on the data processing system is furthermore provided by the present application.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Other storage media include storage in DNA (e.g. in synthesized DNA strands). Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

A Computer Program:

A computer program (product) comprising instructions which, when the program is executed by a computer, cause the computer to carry out (steps of) the method described above, in the 'detailed description of embodiments' and in the claims is furthermore provided by the present application.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

A Hearing System:

In a further aspect, a hearing system comprising a hearing aid as described above, in the 'detailed description of embodiments', and in the claims, AND an auxiliary device is moreover provided.

The hearing system is adapted to establish a communication link between the hearing aid and the auxiliary device to provide that information (e.g. control and status signals, possibly audio signals) can be exchanged or forwarded from one to the other.

The auxiliary device may comprise a remote control, a smartphone, or other portable or wearable electronic device, such as a smartwatch or the like.

The auxiliary device may be constituted by or comprise a remote control for controlling functionality and operation of the hearing aid(s). The function of a remote control is implemented in a smartphone, the smartphone possibly running an APP allowing to control the functionality of the audio processing device via the smartphone (the hearing aid(s) comprising an appropriate wireless interface to the smartphone, e.g. based on Bluetooth or some other standardized or proprietary scheme).

The auxiliary device may be constituted by or comprise an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing aid.

The auxiliary device may be constituted by or comprise another hearing aid. The hearing system may comprise two hearing aids adapted to implement a binaural hearing system, e.g. a binaural hearing aid system.

For example, the hearing system may comprise an auxiliary device, e.g. a wearable configured to determine the PTT and provide the determined PTT to the hearing aid.

PPG measurements are highly energy consuming and may have a significant impact on the hearing aid battery lifetime. A high energy consumption may be due to a constant data acquisition and processing and powering of the LEDs used to illuminate and sense the blood flow.

Accordingly, for example, the computation and energy resource asymmetry in Body Area Networks may be exploited, such that the constant data acquisition and processing and the powering of the LEDs may be delegated to other wearables (e.g. a smartwatch) and provided to the hearing aid via a common gateway (e.g. the mobile phone). Determining the PTT may then be either fully offloaded to the wearable and used as an input to the hearing aid or determined cooperatively, such that PTT may be determined through an electrical measurement of the pulse at the wearable and via a PPG sensor at the hearing aid (or vice-versa) and assuming synchronized measurements (see below). This allows to determine PTT in several configurations: two hearing aids and one wearable or one hearing aid and one wearable.

Further, PTT measurements carried out by hearing aids may be complemented with measurements from a second source, e.g. an auxiliary device (such as a wearable). Thereby, the robustness of the measurements may be increased and the signal processing may be simplified.

For example, PPG sensors may be present in many other wearable products, for example smart watches. The different body placements of other PPG-capable wearables may make them ideal to acquire additional PTT measurements with the objective of deriving listening effort. However, the challenge here may be the time synchronization between the readings taken across wearables. Time synchronization could be achieved by using a new Bluetooth Low Energy (BLE) service. This would require implementation of the BLE service in the peripherals conducting the data acquisition (i.e. the hearing aids and the smart watch) as well as in the BLE master providing the master notion of time to synchronize the measurements (e.g. the users mobile phone).

For example, possible means of synchronization between hearing aids and/or the auxiliary device may comprise:
Synchronizing PPG sensors in hearing aids: By using the already existing Near Link (NL) system embedded in the hearing aid, the maximum drift would be between 10 to 100 us between hearing aids. This would provide a common notion of time accurate enough for PTT measurements.
Synchronizing PPG sensors in hearing aids and PPG sensors in wearables: To synchronize the PPG measurements from a hearing aid and a wearable, one could implement clock synchronization via a BLE service as mentioned above (e.g CheepSync5 or similar technique). The maximum time drift using techniques of these characteristics could be as low as 10 us.

An APP:

In a further aspect, a non-transitory application, termed an APP, is furthermore provided by the present disclosure. The APP comprises executable instructions configured to be executed on an auxiliary device to implement a user interface for a hearing aid or a hearing system described above in the 'detailed description of embodiments', and in the claims. The APP is configured to run on cellular phone, e.g. a smartphone, or on another portable device allowing communication with said hearing aid or said hearing system.

Definitions

In the present context, a 'hearing device' refers to a device, such as a hearing aid, e.g. a hearing instrument, or an active ear-protection device, or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing aid may be configured to be worn in any known way, e.g. as a unit arranged behind the ear with a tube leading radiated acoustic signals into the ear canal or with an output transducer, e.g. a loudspeaker, arranged close to or in the ear canal, as a unit entirely or partly arranged in the pinna and/or in the ear canal, as a unit, e.g. a vibrator, attached to a fixture implanted into the skull bone, as an attachable, or entirely or partly implanted, unit, etc. The hearing aid may comprise a single unit or several units communicating (e.g. acoustically, electrically or optically) with each other. The loudspeaker may be arranged in a housing together with other components of the hearing aid, or may be an external unit in itself (possibly in combination with a flexible guiding element, e.g. a dome-like element).

More generally, a hearing aid comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit (e.g. a signal processor, e.g. comprising a configurable (programmable) processor, e.g. a digital signal processor) for processing the input audio signal and an output unit for providing an audible signal to the user in dependence on the processed audio signal. The signal processor may be adapted to process the input signal in the time domain or in a number of frequency bands. In some hearing aids, an amplifier and/or compressor may constitute the signal processing circuit. The signal processing circuit typically comprises one or more (integrated or separate) memory elements for executing programs and/or for storing parameters used (or potentially used) in the processing and/or for storing information relevant for the function of the hearing aid and/or for storing information (e.g. processed information, e.g. provided by the signal processing circuit), e.g. for use in connection with an interface to a user and/or an interface to a programming device. In some hearing aids, the output unit may comprise an output transducer, such as e.g. a loudspeaker for providing an air-borne acoustic signal or a vibrator for providing a structure-borne or liquid-borne acoustic signal. In some hearing aids, the output unit may comprise one or more output electrodes for providing electric signals (e.g. to a multi-electrode array) for electrically stimulating the cochlear nerve (cochlear implant type hearing aid). The hearing aid may comprise a speakerphone (comprising a number of input transducers and a number of output transducers), e.g. for use in an audio conference situation.

In some hearing aids, the vibrator may be adapted to provide a structure-borne acoustic signal transcutaneously or percutaneously to the skull bone. In some hearing aids, the vibrator may be implanted in the middle ear and/or in the inner ear. In some hearing aids, the vibrator may be adapted to provide a structure-borne acoustic signal to a middle-ear bone and/or to the cochlea. In some hearing aids, the vibrator may be adapted to provide a liquid-borne acoustic signal to the cochlear liquid, e.g. through the oval window. In some hearing aids, the output electrodes may be implanted in the cochlea or on the inside of the skull bone and may be adapted to provide the electric signals to the hair cells of the cochlea, to one or more hearing nerves, to the auditory brainstem, to the auditory midbrain, to the auditory cortex and/or to other parts of the cerebral cortex.

A hearing device, e.g. a hearing aid, may be adapted to a particular user's needs, e.g. a hearing impairment. A configurable signal processing circuit of the hearing aid may be adapted to apply a frequency and level dependent compressive amplification of an input signal. A customized frequency and level dependent gain (amplification or compression) may be determined in a fitting process by a fitting system based on a user's hearing data, e.g. an audiogram, using a fitting rationale (e.g. adapted to speech). The frequency and level dependent gain may e.g. be embodied in processing parameters, e.g. uploaded to the hearing aid via an interface to a programming device (fitting system), and used by a processing algorithm executed by the configurable signal processing circuit of the hearing aid.

A 'hearing system' refers to a system comprising one or two hearing aids, and a 'binaural hearing system' refers to a system comprising two hearing aids and being adapted to cooperatively provide audible signals to both of the user's ears. Hearing systems or binaural hearing systems may further comprise one or more 'auxiliary devices', which communicate with the hearing aid(s) and affect and/or benefit from the function of the hearing aid(s). Such auxiliary devices may include at least one of a remote control, a remote microphone, an audio gateway device, an entertainment device, e.g. a music player, a wireless communication device, e.g. a mobile phone (such as a smartphone) or a tablet or another device, e.g. comprising a graphical interface. Hearing aids, hearing systems or binaural hearing systems may e.g. be used for compensating for a hearing-impaired person's loss of hearing capability, augmenting or protecting a normal-hearing person's hearing capability and/or conveying electronic audio signals to a person. Hearing aids or hearing systems may e.g. form part of or interact with public-address systems, active ear protection systems, handsfree telephone systems, car audio systems, entertainment (e.g. TV, music playing or karaoke) systems, teleconferencing systems, classroom amplification systems, etc.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include micro-electronic-mechanical systems (MEMS), integrated circuits (e.g. application specific), microprocessors, microcontrollers, digital signal processors (DSPs), field programmable gate arrays (FPGAs), programmable logic devices (PLDs), gated logic, discrete hardware circuits, printed circuit boards (PCB) (e.g. flexible PCBs), and other suitable hardware configured to perform the various functionality described throughout this disclosure, e.g. sensors, e.g. for sensing and/or registering physical properties of the environment, the device, the user, etc. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

Figure 1A:
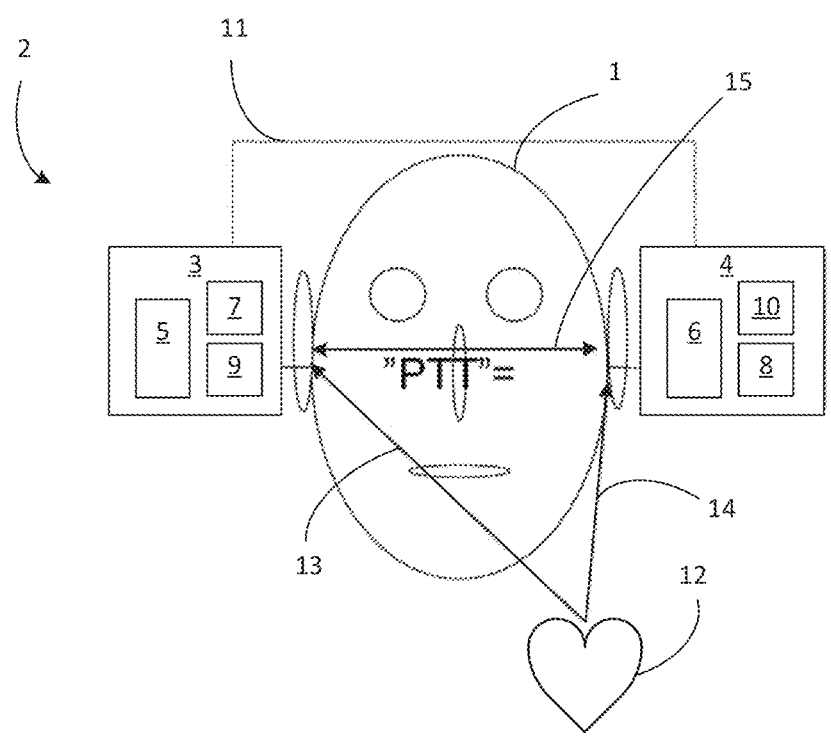
FIG. 1A shows an exemplary application scenario of a system according to the present disclosure.

FIG. 1A shows an exemplary application scenario of a system according to the present disclosure.

In FIG. 1A, a hearing aid user 1 is shown. The hearing aid user 1 is wearing a system 2 (e.g. a hearing aid system). The system 2 of FIG. 1A comprises a first hearing aid 3 in the right ear and a second hearing aid 4 in the left ear. However, systems further comprising e.g. an auxiliary device or comprising only one hearing aid and one or more auxiliary devices may also be contemplated.

The first hearing aid 3 and the second hearing aid 4 may be configured to be worn by the user 1 at or in an ear of the user 1 or to be fully or partially implanted in the head of the hearing aid user 1.

The first hearing aid 3 and the second hearing aid 4 may comprise an input unit (not shown) for receiving an input sound signal from an environment of a hearing aid user 1 and provide at least one electric input signal representing said input sound signal.

The first hearing aid 3 and the second hearing aid 4 may comprise an output unit (not shown) for providing at least one set of stimuli perceivable as sound to the hearing aid user 1 based on processed versions of said at least one electric input signal.

The first hearing aid 3 and the second hearing aid 4 may each comprise a signal processing unit 5,6. The signal processing unit 5,6 may be connected to said input unit and to said output unit and comprise signal processing parameters of the system 2 to provide processed versions of said at least one electric input signal.

The first hearing aid 3 and the second hearing aid 4 may each comprise an SNR estimator (not shown) for determining an SNR in the environment of the system 2.

The first hearing aid 3 and the second hearing aid 4 may each comprise a memory unit (not shown) configured to store reference sets of SNR and PTT of the hearing aid user 1.

However, it is contemplated that only one of the first and the second hearing aids 3,4 comprises a processing unit, an SNR estimator, and/or a memory unit.

For example, said processing unit, SNR estimator, and/or memory unit may comprise signal processing parameter, determine SNR, and store reference set of SNR and PTT, respectively, for both of the first hearing aid 3 and the second hearing aid 4.

The first hearing aid 3 or the second hearing aid 4 may comprise a physiological sensor.

The first hearing aid 3 and the second hearing aid 4 may each comprise a physiological sensor. For example, the physiological sensor may refer to an ECG sensor, a PPG sensor, and/or an EEG sensor.

The physiological sensor may be configured to be in contact with the skin of the external ear canal of the hearing aid user 1, when the hearing aid user 1 is wearing the system 2.

In FIG. 1A, the first hearing aid 3 and the second hearing aid 4 is show to each comprise a PPG sensor 7,8.

The first hearing aid 3 or the second hearing aid 4 may comprise a synchronisation unit.

The first hearing aid 3 and the second hearing aid 4 may each comprise a synchronisation unit.

In FIG. 1A, the first hearing aid 3 and the second hearing aid 4 is show to each comprise a synchronization unit 9,10.

Audio synchronization, by the synchronization units 9,10, across the first hearing aid 3 and the second hearing aid 4 may be useful to synchronize both PPG signals as the sample rate for these PPG signals may be ~250 Hz.

Each of the first 3 and second hearing aids 4 may include an antenna (not shown) and a transceiver circuitry (not shown) for establishing a communication link 11 (wired or wireless) to the other hearing aid, and thereby allowing the exchange of information between the two hearing aids 3,4.

Thus, as illustrated in FIG. 1A, the system 1 may be configured to determine, by the PPG sensor 7 of the first hearing aid 3, the heartbeat of the heart 12 of the user 1. Additionally, the system 1 may be configured to determine, by the PPG sensor 8 of the second hearing aid 4, the heartbeat of the heart 12 of the user 1.

For example, in case the system 1 comprises an ECG sensor for determining the heartbeat at the heart 12 of the user 1, a PTT may be determined based on each of the PPG sensors 7,8, that is a first PPT 13 and a second PTT 14.

Based on the PPG sensor 7 of the first hearing aid 3 and the PPG sensor 8 of the second hearing aid 4, the system may be configured to determine the ear-to-ear PTT 15, which is the time delay of the arrival of pulse between the two ears of the hearing aid user 1.

Figure 1B:
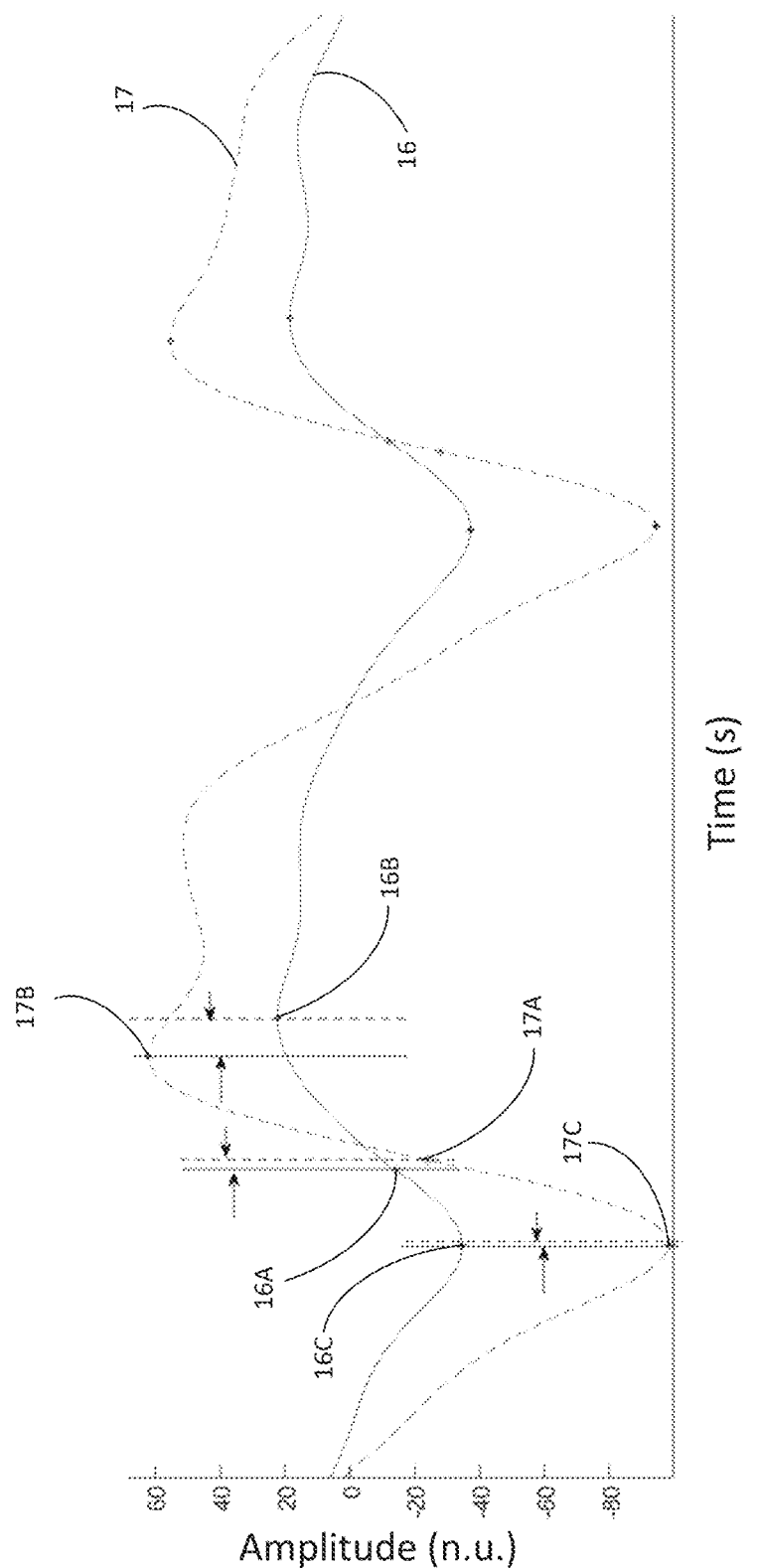
FIG. 1B shows an exemplary ear-to-ear determination of a system according to the present disclosure.

FIG. 1B shows an exemplary ear-to-ear determination of a system according to the present disclosure.

In FIG. 1B, a section of PPG (amplitude as a function of time) 16 determined by the PPG sensor 7 of the first hearing aid 3 and PPG 17 determined by the PPG sensor 8 of the second hearing aid 4, respectively, is plotted.

The required ear-to-ear PTT (BinPTT) may be determined in a number of different ways.

In one way (as indicated), the time delay between the first point in time at a first maximum upslope point 16A of a first measured parameter (determined by the PPG sensor 7 of the first hearing aid 3) and a second point in time at a second maximum upslope point 17A of a second measured parameter (determined by the PPG sensor 8 of the second hearing aid 4), may be the required ear-to-ear PTT.

In a second way, the time delay between the systolic (maximum) point 16B determined by the PPG sensor 7 of the first hearing aid 3 and the systolic (maximum) point 17B determined by the PPG sensor 8 of the second hearing aid 4, may be the required ear-to-ear PTT.

In a third way, the time delay between the foot 16C of the amplitude determined by the PPG sensor 7 of the first hearing aid 3 and the foot 17C of the amplitude determined by the PPG sensor 8 of the second hearing aid 4, may be the required ear-to-ear PTT.

Figure 2:
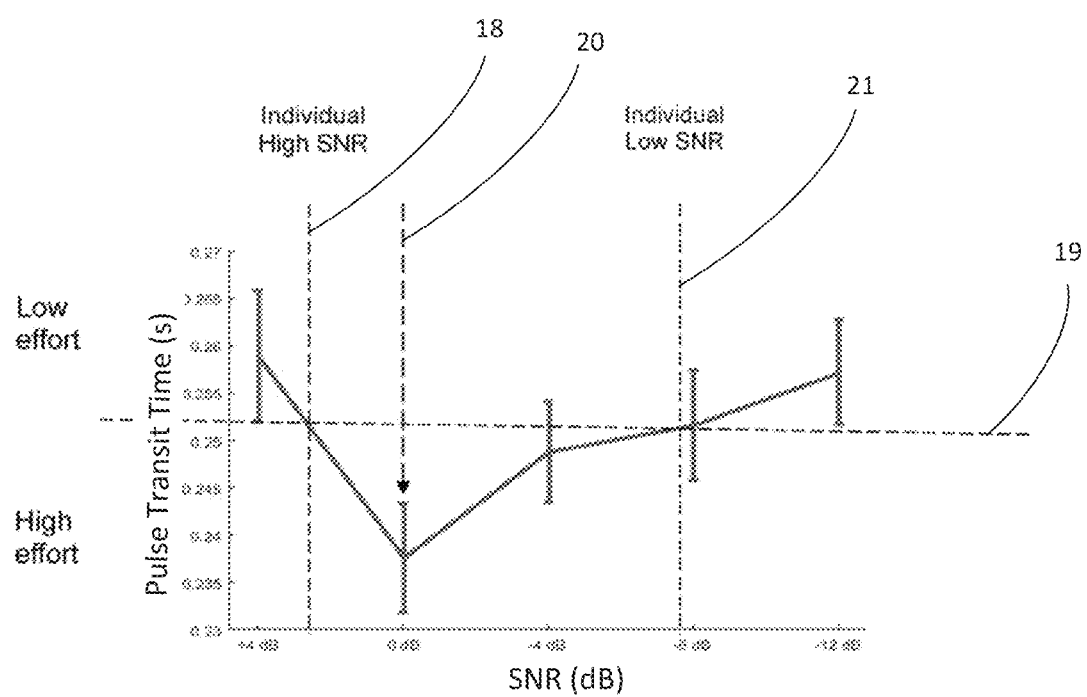
FIG. 2 shows an exemplary monitoring of listening effort based on PTT of a system according to the present disclosure.

FIG. 2 shows an exemplary monitoring of listening effort based on PTT of a system according to the present disclosure.

In FIG. 2, the PTT is illustrated as a function of the SNR level.

An experiment was designed to estimate the listening effort based on physiological sensors data in a speech in noise test. Test subjects were embedded with ECG, PPG sensors in the ears and Pupil glasses to capture the pupil dilation.

Two reference measures of listening effort were recorded in the experiment: Cardiac Pre-ejection (PEP) period [2] and Pupil dilation [3]. The PEP period may be defined as the time delay between the Q point of an ECG and the B point of an Impedence cardiography (ICG) signal.

Pupil dilation is a golden standard for estimating listening effort and therefore may be a reference for any physiological measurement which can be interpreted as an outcome of listening effort. Similarly, PEP period is a pure sympathetic measure of cardiac rhythm, which is also correlated to the listening effort.

It was seen that the ear level PTT was correlated with listening effort when evaluated against the corresponding pupil dilation and PEP.

Both PEP and pupil dilation measures show the maximum effort around 0 dB and 'giving up' when the listening conditions are very demanding (SNR below 0 dB).

By analysing the individual hearing aid user profile of PTT vs SNR in the system, it will be possible to monitor the 'giving up' point as shown in FIG. 2.

This analysis may be used in at least two ways.

In a first way, if the user has passed a giving-up point—(at SNRs lower than the user wants to invest in) the system processing unit may be configured to reduce the required listening effort of the hearing aid user. For example, processing unit may apply beamforming, noise reduction (e.g. by providing separation of noise and speech by machine learning (e.g. by a deep neural network)).

In a second way, if the user has spent long time at 'giving up' SNRs, the system (e.g. the processing unit) may provide advice on what to do (e.g. coping already known strategies for moving to a better SNR region, which may be estimated based on the input from the direction of arrival of sound, the received signal strength in the hearing aid antenna, and the magnetic field map, where the hearing aid is less affected by magnetic interference).

In FIG. 2, the determination of the current listening effort is illustrated. The current listening effort may comprise to determine a current listening difficulty area.

Four listening difficulty areas may be defined.

A first listening difficulty area may be defined as having an SNR above a first SNR threshold 18 and a PTT above a first PTT threshold 19. For example, in the first area, the PTT may be decreasing as a function of decreasing SNR. The first area may be indicative of the hearing aid user providing only little listening effort, as the SNR is high.

A second listening difficulty area may be defined as having an SNR below the first SNR threshold 18, and above a second SNR threshold 20, and a PTT below the first PTT threshold 19. For example, in the second area, the PTT may be decreasing as a function of decreasing SNR. The second area may be indicative of the hearing aid user is providing an increasing listening effort.

A third listening difficulty area may be defined as having an SNR below the second SNR threshold 20, and above a third SNR threshold 21, and a PTT below the first PTT threshold 19. For example, in the third area, the PTT may be increasing as a function of decreasing SNR. The third area may be indicative of the hearing aid user starting to disengage and providing a decreasing listening effort.

A fourth listening difficulty area may be defined as having an SNR below the third SNR threshold 21 and a PTT above the first PTT threshold 19. For example, in the fourth area, the PTT may be increasing as a function of decreasing SNR. The fourth area may be indicative of the hearing aid user completely disengaging and providing minimal listening effort.

The system (the processing unit) may be configured to be in a first listening mode when the current listening difficulty area is the first area, a second listening mode when the current listening difficulty area is the second area, a third listening mode when the current listening difficulty area is the third area, and in a fourth listening mode when the current listening difficulty area is the fourth area.

Figure 3:
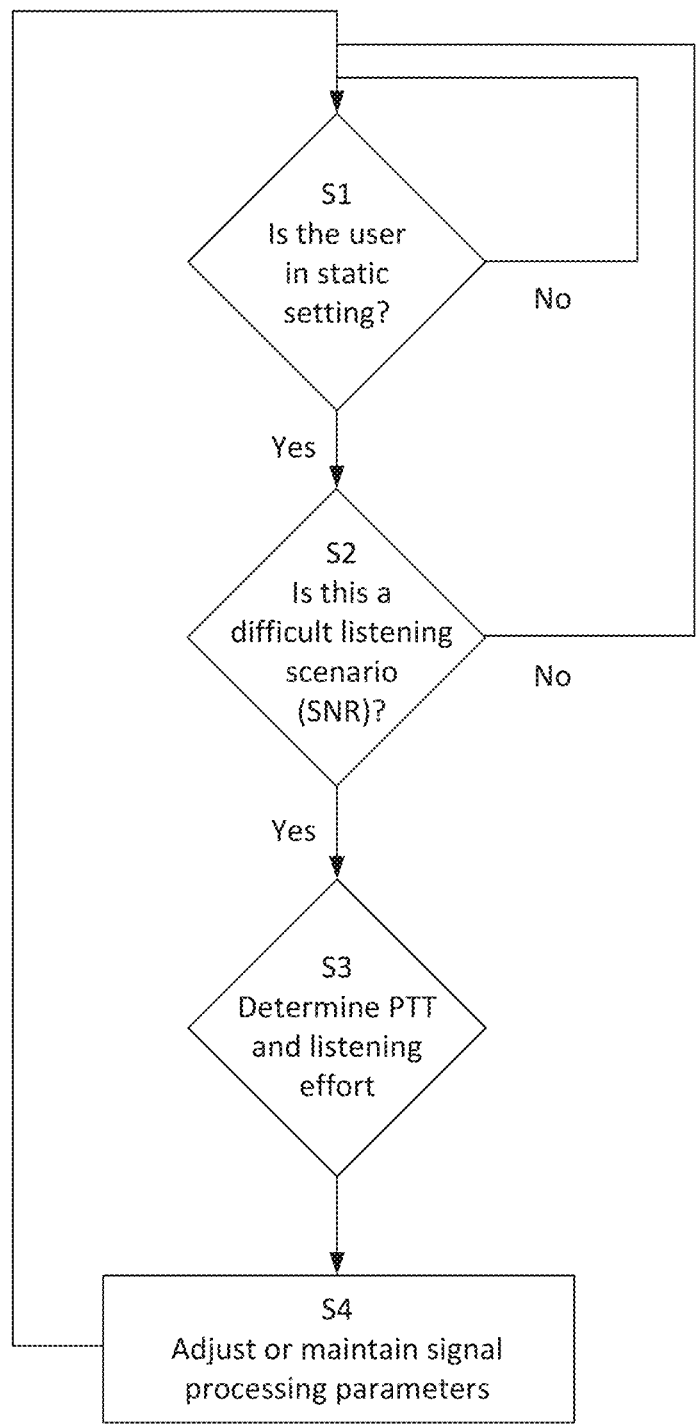
FIG. 3 shows an exemplary flow diagram of an application scenario of a system according to the present disclosure.

FIG. 3 shows an exemplary flow diagram of an application scenario of a system according to the present disclosure.

An additional technique to decrease the sensor power consumption over time may be to activate the PPG sensor(s) only when the relevant event to be sensed is expected, in this case the point in the upslope that is relevant to PTT measurements in the PPG readings. In between consecutive readings, the PPG sensor may be completely turned off or in a low power consumption mode (in case this is provided by the sensor(s)). Naturally, as the heartrate of the hearing aid user varies over time depending on different physiological factors, this "sleeping window" has to be adjusted accordingly, such that relevant measurement points are not lost. Further, reduction of power consumption may be achieved by not determining the PTT for every heartbeat, but only periodically. The application of this additional power reduction strategy may be subject to accuracy and resolution requirements of the algorithm behind the flow diagram as shown in FIG. 3.

The system may determine S1, by the at least one accelerometer, whether the hearing aid user is in a static setting, in other words, whether the hearing aid user is standing still or at least moving less than a predetermined threshold (e.g. a first movement threshold). If not, this step S1 may be repeated (e.g. with a predetermined time interval).

The system may determine S2, by the at least one SNR estimator (for example, by the microphone(s) of the at least one input unit), whether the environment in which the hearing aid user is in, is a difficult listening scenario (for example, the SNR is below a threshold (e.g. 0 dB)). If not, this step S2 may be repeated (e.g. with a predetermined time interval).

In case the first step S1 and the second step S2 are fulfilled, the system may be configured to activate (or maintain is already activated) the at least first and second physiological sensor. Thereby, the system may determine S3 the ear-to-ear PTT and the current listening effort of the hearing aid user.

Depending on the current listening effort, the system may adjust or maintain S4 the signal processing parameters of the processing unit of the system (depending on the current signal processing parameters). The steps S1,S2,S3,S4 may be repeated, for example, after a predetermined time interval.

In case the first S1 and/or the second S2 steps are not fulfilled, the system may be configured to change the activation mode of the at least first and second physiological sensor (e.g. to deactivate already activated sensors).

Figure 4A:
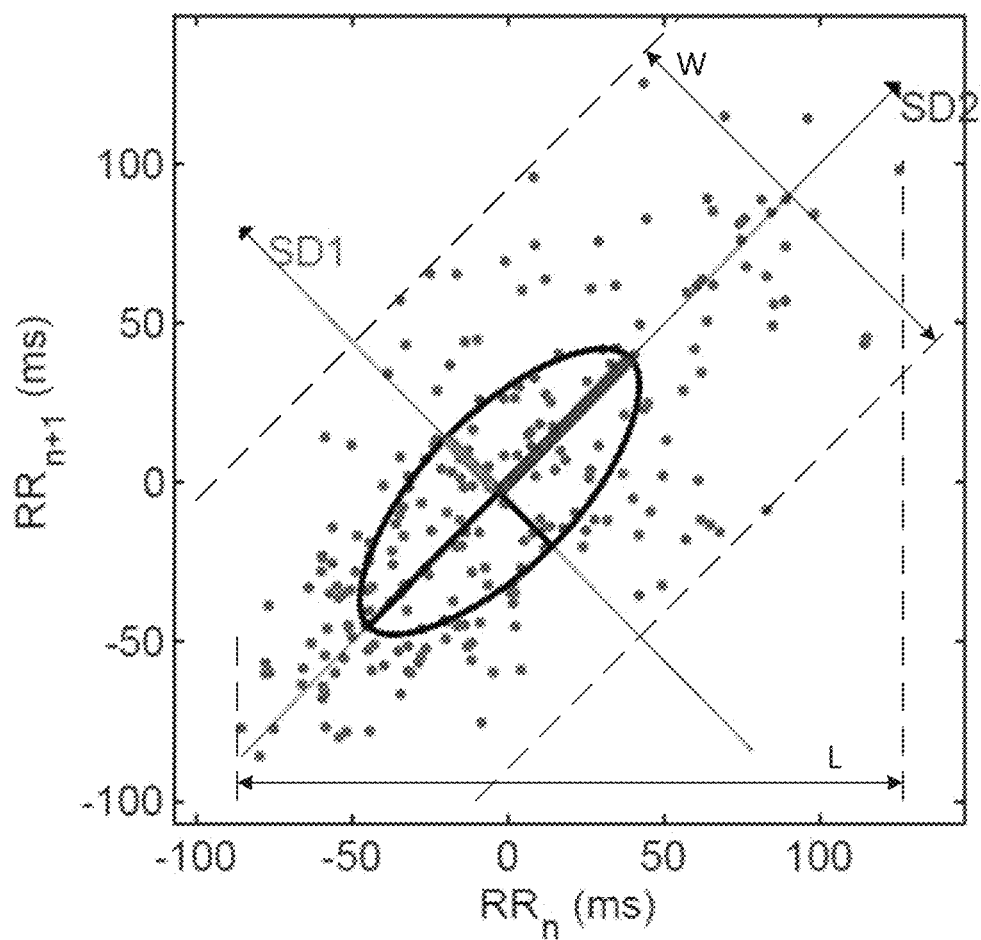
FIG. 4A shows a Poincaré plot of an exemplary application scenario of a system according to the present disclosure.
Figure 4B:
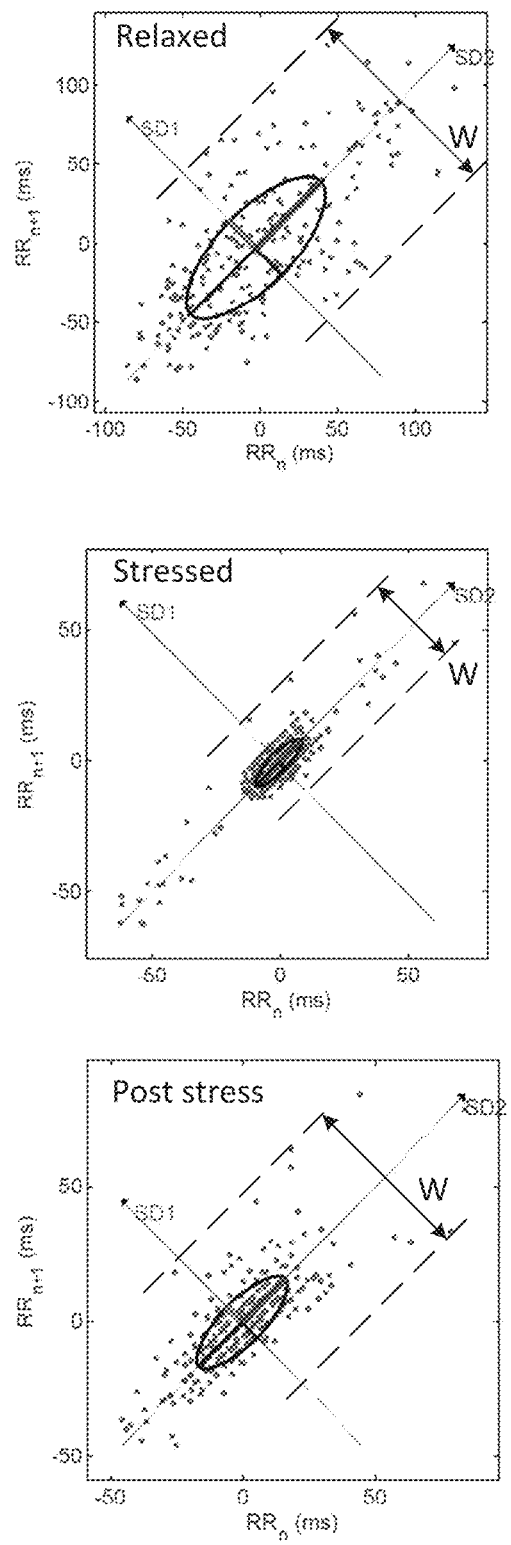
FIG. 4B shows an exemplary application scenario of a system according to the present disclosure.
Figure 4C:
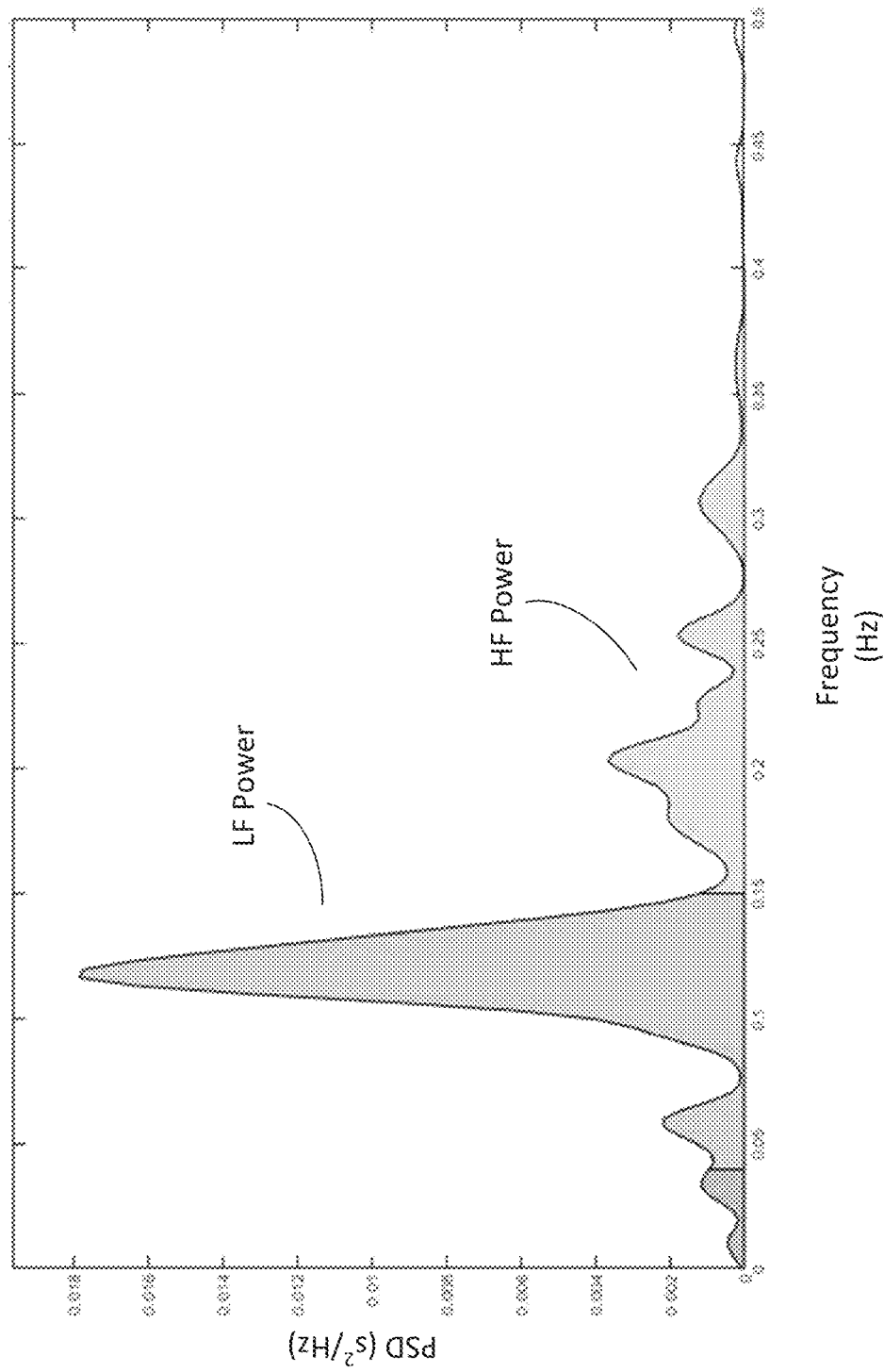
FIG. 4C shows a frequency spectrum of an exemplary application scenario of a system according to the present disclosure.

FIGS. 4A, 4B, and 4C shows an exemplary application scenario of a system according to the present disclosure.

If there was a reliable way to automatically detect an increased listening effort by the hearing aid user, for instance when he/she is trying to follow a conversation in a difficult sound environment, the hearing aid (system) software (or connected smartphone app) may act on it by dynamically regulating the hearing aid parameters (signal processing parameters) in order to help the user.

The solution may be based on the combination of different inputs and may be based on a known correlation between stress/effort and heart rate variability: if an end-user (e.g. a hearing device user) is under stress/effort, it is possible to do analysis on the heart rate variability signal of this end-user and identify stress indexes.

Pulse rate and heart rate variability may be measured via the hearing aid, for example by means of an optical sensor placed in the hearing aid speaker unit (e.g. in-ear PPG sensor). Alternatively, heart rate and heart rate variability may also be measured by means of an accelerometer placed in the hearing aid. However, it should be noted that measuring heart rate variability from an accelerometer is more prone to motion artefacts than using a pulse oximeter.

Acute stress may have many different causes—listening effort being one of them. For instance, a person may be trying to solve a mathematical problem, undergo a job interview, give a public speech, etc. It may be possible to estimate the level of acute stress by looking into the Autonomic nervous system (ANS) activity of the end-user under certain circumstances.

We may estimate the ANS activity of the end-user by analysing the Heart Rate Variance (HRV).

The ANS branches: Sympathetic Nervous System (SNS) and Parasympathetic Nervous System (PNS), are responsible for the sympatho-vagal balance [4]. The dynamics of the heart rate is influenced by both the SNS and PNS activity. Therefore, the HRV signal may be a good indicator of ANS activity which may also reflect a certain state of stress.

HRV may be analysed both in the time domain and in the frequency domain to quantify SNS and PNS estimates and implicitly to estimate stress.

Time Domain Features:

In the time domain, the Poincaré plot analysis is a geometrical and nonlinear method to assess the dynamics of HRV. In this plot, successive heart rates are plotted to each other, resulting in a cloud of points. The clouds of points are then mapped to an ellipse and the width of the ellipse is a measure of the short-term variability, which is reflected as parasympathetic influence. The length of the ellipse is known as total variability.

SD is the standard deviation operator. The SD1 and SD2 are calculated by [5], $$SD1 = \frac{1}{\sqrt{2}} SD(x_n - x_{n+1})$$

$$SD2 = \sqrt{2SD(x_n^2) - \frac{1}{2}SD(x_n - x_{n+1})^2}$$

During a stress state, parasympathetic influence is suppressed and sympathetic influence is dominant, hence the width of the Poincare plot will decrease during stress.

In FIG. 4A, an illustrative example of a Poincare plot is shown. On the X-axis, the interval between consecutive heartbeats at time k is shown and on the Y-axis the interval between consecutive heartbeats at time k+1 is shown ("RR" is the time interval between successive R peaks of an ECG wave or may be an Inter Beat Interval (IBI) parameter defining the time between consecutive heartbeats of a PPG signal). The width (W) and corresponding standard deviation (SD1) as well as the length (L) and corresponding standard deviation (SD2) of the plot are indicated.

In FIG. 4B, an example of how the Poincare estimate of stress is determined is shown. The heart rate variability on a hearing aid user may be measured with a paradigm of: 1 minute rest, 1 minute physical stress and 1 minute rest. In FIG. 4B, it is shown how the width and corresponding SD1 of the Poincare plot under these three scenarios, i.e. a relaxed state (top), a stressed state (middle), and a post stress state (bottom), may change significantly.

Frequency Domain Features:

In FIG. 4C, it is shown that the Low Frequency (LF) and High Frequency (HF) component of the frequency spectrum of HRV reflect the SNS and PNS activity. The LF (0.04-0.15 Hz) component of HRV reflects both the SNS and PNS activity, while the HF component of HRV reflects purely PNS activity. Therefore, the ratio LF/HF is an estimate of stress.

Listening Induced Stress:

Heart rate variability parameters may manifest significant of listening effort on a hearing aid user (not significant on the normal hearing) [6]. The parasympathetic marker of HRV (HF power) was decreasing as the listening conditions were tending to be more and more difficult.

From HRV, the ANS parameters SD1, SD2, SD1/SD2, LF (power), HF (Power), LF/HF may be determined. Since HRV dynamics is not instantaneous, hence, a duration of at least 60 seconds data is required [7]. A classifier (LDA, naive bias, etc) may be developed based on those parameters to identify stress/non-stress condition based on individual baseline.

Accordingly, the hearing aid may be configured to, when there is a high listening effort, reduce the listening effort the hearing aid user. Once a time series of Poincare widths is determined, situations with high listening effort requirements may be identified by combining this HRV measure with other objective measures that can infer stress, such as:

The SNR of the surrounding sound environment (measured using e.g. the hearing aid microphones)

The relatively elevated sound pressure level at typical speech frequencies ("speech in noise") The user movement (or lack thereof) detected by an accelerometer embedded in the hearing aid.

The person is not talking—but mainly listening (own voice may be detected with good approximation from the hearing aid sound input, possibly corroborated by accelerometer data (e.g. measured by an in-ear accelerometer)).

HRV may be affected by many factors: running, doing an exam, etc. However, not all these cases would necessarily mean that the hearing aid user is under an effortful listening task. By combining HRV analysis with the above-mentioned other sound-related objective indicators, it is possible to estimate a high listening demanding task and to adapt the hearing aid to minimize those (e.g., maximize the Poincare width).

There are other methods to analyze the HR with the aim of estimating the stress level of the end-user under a certain situation. The exemplary application provided in FIGS. 4A-4C with the Poincare plot may be applied to combine a HR variability measure with one or more other measures to identify high demanding listening situations and adapt the hearing aid signal processing parameters accordingly.

Accordingly, a system comprising a hearing aid, where the hearing aid may be configured to be operated based on an estimation of a current listening effort of a hearing aid user (as stated above) may be provided, where the determination of a current listening effort of the hearing aid user may be carried out based on determining HRV of the hearing device user as stated above.

It is intended that the structural features of the system/devices/aids described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein but are to be accorded the full scope consistent with the language of the claims, wherein reference to an element in the singular is not intended to mean "one and only one" unless specifically so stated, but rather "one or more". Unless specifically stated otherwise, the term "some" refers to one or more.

Accordingly, the scope should be judged in terms of the claims that follow.

REFERENCES

[1] S. Hey, A. Gharbi, B. v. Haaren, K. Walter, N. Konig and S. Löffler, "Continuous Noninvasive Pulse Transit Time Measurement for Psycho-physiological Stress Monitoring," 2009 International Conference on eHealth, Telemedicine, and Social Medicine, Cancun, 2009, pp. 113-116. doi: 10.1109/eTELEMED.2009.35
[2] Richter M. The moderating effect of success importance on the relationship between listening demand and listening effort. Ear and Hearing. 2016; 37:111S-117S. doi: 10.1097/AUD.0000000000000295
[3] Ohlenforst, B., Zekveld, A. A., Lunner, T., Wendt, D., Naylor, G., Wang, Y., Versfeld, N.J., Kramer, S. E., 2017. Impact of stimulus-related factors and hearing impairment on listening effort as indicated by pupil dilation. Hear. Res. 351, 68e79
[4] Goldberger J J. Sympathovagal balance: how should we measure it?. Am J Physiol. 1999 April; 276(4 Pt 2):H1273-80.
[5] Hoshi, R. A., Pastre, C. M., Vanderlei, L. C. M., & Godoy, M. F. (2013). Poincare plots indexs of heart rate variability: relationship with other nonlinear variables. Autonomic neuroscience.
[6] Hsu C H, Tsai M Y, Huang G S, Poincaré plot indexes of heart rate variability detect dynamic autonomic modulation during general anesthesia induction. Acta Anaesthesiol Taiwan. 2012 March; 50(1):12-8
[7] Esco M R, Flatt A A, Ultra-short-term heart rate variability indexes at rest and post-exercise in athletes: evaluating the agreement with accepted recommendations. J Sports Sci Med. 2014 Sep. 1; 13(3):535-41. eCollection 2014 September

The invention claimed is:

1. A hearing aid configured to be operated based on an estimation of a current listening effort of a hearing aid user, the hearing aid comprising
an input unit for receiving an input sound signal from an environment of the hearing aid user and providing at least one electric input signal representing said input sound signal,
an output unit for providing at least one set of stimuli perceivable as sound to the hearing aid user based on processed versions of said at least one electric input signal,
a processing unit connected to said input unit and to said output unit and comprising signal processing parameters to provide processed versions of said at least one electric input signal,
at least one physiological sensor,
wherein the hearing aid is configured to determine a current listening effort of the hearing aid user based on determining Heart Rate Variability (HRV) of the hearing aid user, and
wherein the hearing aid comprises a signal-to-noise ratio (SNR) estimator for determining an SNR in the environment of the hearing aid user.

2. The hearing aid according to claim 1, wherein the HRV is determined based on the at least one physiological sensor.

3. The hearing aid according to claim 1, wherein the hearing aid comprises at least one accelerometer configured to detect a movement of the hearing aid user.

4. The hearing aid according to claim 1, wherein the hearing aid comprises an own voice detector.

5. The hearing aid according to claim 1, wherein determining the current listening effort comprises analysing the HRV in the time domain and/or in the frequency domain.

6. The hearing aid according to claim 5, wherein determining the current listening effort further comprises one or more of determining movement of the hearing aid user by the accelerometer, determining the SNR in the environment of the hearing aid user by the SNR estimator, and detecting own voice of the hearing aid user by the own voice detector.

7. The hearing aid according to claim 5, wherein analysing the HRV in the time domain comprises determining a width and/or a length of the HRV in a Poincaré plot.

8. The hearing aid according to claim 5, wherein analysing the HRV in the frequency domain comprises determining a ratio of the power in a low frequency band to the power in a high frequency band of a frequency spectrum of the HRV.

9. The hearing aid according to claim 1, wherein the hearing aid is configured to adjust the signal processing parameters of the processing unit based on the determined current listening effort.

10. The hearing aid according to claim 1,
wherein the hearing aid is configured to determine whether an activation requirement is fulfilled, the activation requirement comprising that
the movement detected by the accelerometer is below a movement threshold, and
the SNR is below another threshold, and
wherein, in response to the activation requirement being fulfilled, the processing unit is configured to change the activation mode of the at least one physiological sensor.

11. The hearing aid according to claim 10, wherein, configured to change the activation mode of the at least one physiological sensor, comprises configured to activate at least one physiological sensor.

12. The hearing aid according to claim 10, wherein, configured to change the activation mode of the at least one physiological sensor, comprises configured to change the activation mode of the at least one physiological sensor from standby mode to operational mode.

13. The hearing aid according to claim 10, wherein, when the activation requirement is not fulfilled, the processing unit is configured to change or maintain the mode of the at least one physiological sensor to the standby mode or a deactivated mode.

14. The hearing aid according to claim 1, wherein the at least one physiological sensor is a photoplethysmogram (PPG) sensor and/or an electrocardiogram (ECG) sensor.

15. A system comprising at least one hearing aid according to claim 1 and an auxiliary device.

16. The system according to claim 15, wherein each of the at least one hearing aid and the auxiliary device are configured to establishing a communication link, and thereby allowing the exchange of information between the at least one hearing aid and the auxiliary device.

17. The system according to claim 15 comprising a first and a second hearing aid each comprising a physiological sensor.

18. A hearing aid configured to be operated based on an estimation of a current listening effort of a hearing aid user, the hearing aid comprising
an input unit for receiving an input sound signal from an environment of the hearing aid user and providing at least one electric input signal representing said input sound signal,
an output unit for providing at least one set of stimuli perceivable as sound to the hearing aid user based on processed versions of said at least one electric input signal,
a processing unit connected to said input unit and to said output unit and comprising signal processing parameters to provide processed versions of said at least one electric input signal,
at least one physiological sensor,
wherein the hearing aid is configured to determine a current listening effort of the hearing aid user based on determining Heart Rate Variability (HRV) of the hearing aid user, and
wherein the hearing aid comprises an own voice detector.

* * * * *